United States Patent [19]

Hoelderich et al.

[11] Patent Number: 4,891,451
[45] Date of Patent: Jan. 2, 1990

[54] PREPARATION OF VINYL ETHERS

[75] Inventors: Wolfgang Hoelderich, Frankenthal; Norbert Goetz, Worms 1; Leopold Hupfer, Friedelsheim, all of Fed. Rep. of Germany

[73] Assignee: BASF Aktiengesellschaft, Ludwigshafen, Fed. Rep. of Germany

[21] Appl. No.: 213,589

[22] Filed: Jun. 30, 1988

[30] Foreign Application Priority Data

Jul. 10, 1987 [DE] Fed. Rep. of Germany ..... 37228919

[51] Int. Cl.$^4$ .............................................. C07C 41/28
[52] U.S. Cl. .................................... 568/691; 568/579; 568/626; 568/663; 568/667; 568/686
[58] Field of Search ............... 568/691, 579, 626, 663, 568/667, 686

[56] References Cited

U.S. PATENT DOCUMENTS

| | | | |
|---|---|---|---|
| 3,702,886 | 11/1972 | Argauer et al. | 423/328 |
| 3,705,924 | 12/1972 | Smith et al. | 568/691 |
| 3,709,973 | 1/1973 | Maltby et al. | 264/244 |
| 4,208,305 | 6/1980 | Kouwenhoven et al. | 252/431 N |
| 4,238,318 | 12/1980 | Kouwenhoven et al. | 208/120 |
| 4,268,420 | 5/1981 | Klotz | 252/432 |
| 4,401,637 | 8/1983 | Marosi et al. | 556/27 |
| 4,456,582 | 6/1984 | Marosi et al. | 423/277 |

FOREIGN PATENT DOCUMENTS 039410 4/1987 European Pat. Off. .
2091259 of 0000 United Kingdom .

OTHER PUBLICATIONS

European Search Report.

*Primary Examiner*—Donald B. Moyer
*Assistant Examiner*—Karen E. Plue
*Attorney, Agent, or Firm*—Keil & Weinkauf

[57] ABSTRACT

Vinyl ethers of the formula (I)

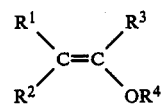

where $R^1$ to $R^3$ are identical or different and are each hydrogen, a straight-chain or branched alkyl or alkenyl radical of not more than 12 carbon atoms, halogen-substituted alkyl, a cycloalkyl or cycloalkenyl radical of 5 to 8 carbon atoms, an aryl, alkylaryl, alkenylaryl, aralkyl or aralkenyl radical of 6 to 16 carbon atoms, halogen-substituted aryl or a heterocyclic radical and furthermore $R^1$ and $R^2$ or $R^1$ and $R^3$, together with the carbon atom to which they are bonded, may form a cycloalkane, cycloalkene or heterocyclic structure, and $R^4$ is alkyl, alkylaryl or aralkyl, are prepared by a process in which an alcohol is eliminated from an acetal or ketal of the formula (II)

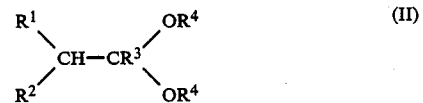

where $R^1$ to $R^4$ have the above meanings, in the presence of borosilicate and/or iron silicate zeolites as catalysts.

3 Claims, No Drawings

PREPARATION OF VINYL ETHERS

The present invention relates to a process for the preparation of vinyl ethers by eliminating an alcohol from an acetal or ketal in the presence of a catalyst.

Vinyl ethers are employed in the preparation of certain homo- and copolymers which are used in the fields of coating and adhesive production and as assistants in the textile and leather industry. Vinyl ethers are also useful intermediates for organic syntheses, for example for Diels-Alder reactions, for the preparation of glutar dialdehydes, γ-pyran and γ-picoline, as well as active ingredients.

Industrially, vinyl ethers are produced by the Reppe method from acetylene and alcohols in the liquid phase using potassium hydroxide as a catalyst. However, acetylene is not available as a starting material at every chemical plant, and an alternative synthesis for vinyl ethers is therefore desirable.

Vinyl ethers can also be prepared by eliminating an alcohol from an acetal. This can be carried out by a purely thermal process or by homogeneous or heterogeneous catalysis. Some of the catalysts used to date are restricted in their range of applications and some have unsatisfactory activity and selectivity and an inadequate life.

It is known that vinyl ethers can be obtained by eliminating an alcohol from an acetal over an aluminosilicate zeolite. These zeolites, in their acidic H form, have unsatisfactory selectivities and conversions. By doping the zeolites with Na, it is only possible to increase the selectivity in conjunction with incomplete conversion.

We have found that vinyl ethers of the formula (I)

where $R^1$ to $R^3$ are identical or different and are each hydrogen, a straight-chain or branched alkyl or alkenyl radical of not more than 12 carbon atoms, halogen-substituted alkyl, a cycloalkyl or cycloalkenyl radical of 5 to carbon atoms, an aryl, alkylaryl, alkenylaryl, aralkyl or aralkenyl radical of 6 to 16 carbon atoms, halogen-substituted aryl or a heterocyclic radical and furthermore $R^1$ and $R^2$ or $R^1$ and $R^3$, together with the carbon atom to which they are bonded, may form a cycloalkane, cycloalkene or heterocyclic structure, and $R^4$ is alkyl, alkylaryl or aralkyl, are obtained in high selectivity with complete conversion from an acetal or ketal, if an alcohol is eliminated from an acetal or ketal of the formula (I)

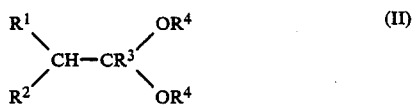

where $R^1$ to $R^4$ have the above meanings, in the presence of a borosilicate and/or iron silicate zeolite as catalysts.

In view of the prior art, the results of the novel process are surprising because the development to date points precisely in the opposite direction, namely the elimination of acidic centers by doping with sodium. Hence, it was not to be expected that borosilicate and/or iron silicate zeolites in the acidic H form would give such excellent results within such wide limits.

Independently of $R^4$, suitable radicals $R^1$ and $R^3$ are hydrogen and straight-chain or branched alkyl of 1 to 12, in particular 1 to 8, preferably 1 to 4, carbon atoms.

Examples of alkyl or alkenyl are methyl, ethyl, n-propyl, isopropyl, propenyl, isopropenyl, n-butyl, isobutyl, n-butenyl, isobutenyl, pentyl, pentenyl, hexyl, hexenyl, heptyl, heptenyl, octyl, octenyl, nonyl, nonenyl, decyl, decenyl, dodecyl and dodecenyl. The alkyl or alkenyl radicals may furthermore carry substituents which are inert under the reaction conditions, for example halogen.

Examples of cycloalkyl are cyclopentyl, cyclohexyl, cycloheptyl, cyclopentenyl and cyclohexenyl.

Examples of suitable aromatic radicals are phenyl, benzyl, 2-phenylethyl, 3-phenylpropyl, 2-phenylpropyl, 4-phenylbutyl, 3-phenylbutyl, 2-phenylbutyl and 3-phenylbutenyl, which may furthermore be substituted by radicals which are inert under the reaction conditions, such as alkyl or halogen.

Suitable radicals $R^4$ are alkyl radicals, such as methyl, ethyl, n-propyl, isopropyl, propenyl, n-butyl, isobutyl, tert-butyl, butenyl, octyl or octenyl, and aralkyl radicals, such as benzyl, phenylethyl or phenylpropyl, and alkylaryl radicals, such as toluyl or xylyl.

Suitable starting materials are acetals of saturated aliphatic aldehydes, for example acetaldehyde, propionaldehyde or butyraldehyde, pentanal, hexanal and higher homologous n-alkanals, such as octanals and decanals, branched aldehydes, such as isobutyraldehyde, 2-methylbutanal, 3-methylbutanal, 3,3-dimethylbutanal, 2-methylpentanal, 2-methylhexanal and 2-methyldecanal.

Examples of suitable ketones for the ketals used are the following compounds: methyl ethyl ketone, diethyl ketone, methyl isopropyl ketone, diisopropyl ketone, diisobutyl ketone, methyl isobutyl ketone, methylcyclohexanone, cyclohexanone, acetophenone and substituted acetophenones.

The catalysts used are borosilicate and/or iron silicate zeolites.

Borosilicate zeolites can be synthesized at from 90° to 200° C. under autogenous pressure by reacting a boron compound, e.g. $H_3BO_3$, with a silicon compound, preferably finely divided silica, in aqueous amine solution, in particular in 1,6-hexanediamine or 1,3-propanediamine or triethylenetetramine solution, with or, in particular, without the addition of an alkali or alkaline earth. These also include the isotactic zeolites according to German Laid-Open Application No. DOS 3,006,471 and European Pat. No. 46,504. Such borosilicate zeolites can also be prepared if the reaction is carried out in ether solution, for example diethylene glycol dimethyl ether, or in alcoholic solution, for example hexane-1,6-diol, instead of in aqueous amine solution.

Iron silicate zeolites are obtained, for example, from an iron compound, preferably $Fe_2(SO_4)_3$, and a silicon compound, preferably finely divided silica, in aqueous amine solution, in particular in 1,6-hexanediamine, with or without the addition of an alkali or alkaline earth, at from 100° to 220° C. under autogenous pressure.

The borosilicate and iron silicate zeolites thus prepared can be isolated, dried at from 100° to 160° C., preferably 110° C., and calcined at from 450° to 550° C., preferably 500° C., and then molded with a binder in a weight ratio of from 90:10 to 40:60 to give extrudates or pellets. Suitable binders are various aluminas, preferably boehmite, amorphous aluminosilicates having an $SiO_2/Al_2O_3$ ratio of from 25:75 to 90:5, preferably 75:25, silica, preferably finely divided $SO_2$, mixtures of finely divided $SiO_2$ and finely divided $Al_2O_3$, $TiO_2$, $ZrO_2$ and clay. After the molding procedure, the extrudates or pellets are dried at 110° C. for 16 hours and calcined at 500° C. for 16 hours.

Very suitable catalysts are also obtained if the iron silicate or borosilicate zeolites isolated are molded directly after drying and not subjected to calcination until after the molding procedure. The iron silicate and borosilicate zeolites prepared can be used in pure form, without a binder, as extrudates or pellets, extrusion or peptizing assistants used being, for example, ethylcellulose, stearic acid, potato starch, formic acid, oxalic acid, acetic acid, nitric acid, ammonia, amines, silicoesters and graphite as well as mixtures of these.

If, because of their method of preparation, the zeolites are not in the catalytically active, acidic H form but, for example, in the Na form, the latter can be completely or partially converted into the desired H form by ion exchange, for example with ammonium ions, followed by calcination, or by treatment with acids.

If, when the zeolite catalysts are used according to the invention, deactivation occurs as a result of coking, it is advisable to regenerate the zeolites by burning off the coke deposits with air or with an air/$N_2$ mixture at from 400° to 550° C., preferably 500° C. As a result, the zeolites retain their initial activity.

By precoking, it is possible to adjust the activity of the catalyst to obtain optimum selectivity with respect to the desired reaction product.

In order to obtain very high selectivity, high conversion and a long catalyst life, it may be advantageous to modify the zeolites. In a suitable method of modifying the catalysts, the unmolded or molded zeolites are doped with metal salts by ion exchange or by impregnation. The metals used are alkaline earth metals, such as Mg, Ca or Sr, metals of main groups 3, 4 and 5, such as Al, Ga, Ge, Sn, Pb or Bi, transition metals of sub-groups 4-8, such as Ti, Zr, V, Nb, Cr, Mo, W, Mn, Re, Fe, Ru, Os, Co, Rh, Ir, Ni, Pd or Pt, transition metals of subgroups 1 and 2, such as Cu, Ag or Zn, and rare earth metals, such as La, Ce, Pr, Nd, Er, Yb and U.

Advantageously, the doping is carried out as follows: the molded zeolite is initially taken in a riser tube and, for example, an aqueous or ammoniacal solution of a halide or of a nitrate of the metals described above is passed over the said zeolite at from 20° to 100° C. Ion exchange of this type can be carried out on the hydrogen, ammonium and alkali metal form of the zeolite. In another possible method of applying the metals to the zeolite, the zeolite material is impregnated with, for example, a halide, a nitrate or an oxide of the metals described above, in aqueous, alcoholic or ammoniacal solution. Both ion exchange and impregnation are followed by one or more drying steps and, if desired, repeated calcination.

In a possible embodiment, $Cu(NO_3)_2.3H_2O$ or $Ni(NO_3)_2.6H_2O$ or $Ce(NO_3)_3.6H_2O$ or $La(NO_3)_2.6H_2O$ or $Cs_2CO_3$ is dissolved in water and this solution is used to impregnate the molded or unmolded zeolite for a certain time (about 30 minutes). Any supernatant solution is freed from water in a rotary evaporator. Thereafter, the impregnated zeolite is dried at about 150° C. and calcined at about 550° C. This impregnation process may be carried out several times in succession in order to obtain the desired metal content.

It is also possible to prepare an aqueous $Ni(NO_3)_2$ solution or ammoniacal $Pd(NO_3)_2$ solution and to suspend the pure zeolite powder therein at from 40° to 100° C. for about 24 hours, while stirring. After the product has been filtered off, dried at about 150° C. and calcined at about 500° C., the zeolite material thus obtained can be further processed with or without a binder to give extrudates, pellets or fluidizable material.

The zeolite in the H form or ammonium form or alkali metal form can be subjected to ion exchange by initially taking the zeolite, in the form of extrudates or pellets, in a column and circulating, for example, an aqueous $Ni(NO_3)_2$ solution or ammoniacal $Pd(NO_3)_2$ solution over the said zeolite at slightly elevated temperatures of from 30° to 80° C. for from 15 to 20 hours. Thereafter, the product is washed thoroughly with water, dried at about 150° C. and calcined at about 550° C. In the case of some metal-doped zeolites, for example Pd-, Cu- or Ni-doped zeolites, an aftertreatment with hydrogen is advantageous.

In another possible method of modification, the molded or unmolded zeolite material is subjected to a treatment with acids, such as hydrochloric acid, hydrofluoric acid and phosphoric acid, and/or steam. In this procedure, zeolites in powder form are advantageously treated with 1 N phosphoric acid for 1 hour at 80° C. After the treatment, the product is washed with water, dried at 110° C. for 16 hours and calcined at 500° C. for 20 hours. In another procedure, zeolites are treated, before or after they have been molded with binders, with a 3-25, in particular 12-20, % strngth by weight aqueous hydrochloric acid, for example for from 1 to 3 hours at from 60° to 80° C. Thereafter, the zeolite treated in this manner is washed with water, dried, and calcined at from 400° to 500° C.

In a particular embodiment of the acid treatment, the zeolite material, before it has been molded, is treated at elevated temperatures with 0.001-2 N, preferably 0.05-0.5N hydrofluoric acid, for example by refluxing for from 0.5 to 5, preferably from 1 to 3, hours. After the zeolite material has been isolated, for example by filtering it off and washing it thoroughly, it is advantageously dried at from 100° to 160° C. and calcined at from 450° to 600° C. In another preferred embodiment of the acid treatment, the zeolite material is molded with a binder and then treated at elevated temperatures, advantageously from 50° to 90° C., preferably from 60° to 80° C., for from 0.5 to 5 hours, preferably with 12-20% strength by weight hydrochloric acid. The zeolite material is then washed thoroughly and advantageously dried at from 100° to 160° C. and calcined at from 450° to 600° C. An HF treatment may be followed by an HCl treatment.

In another procedure, zeolites can be modified by applying phosphorus compounds, such as trimethoxy phosphate, trimethoxyphosphine or primary, secondary or tertiary sodium phosphate. Treatment with primary sodium phosphate has proven particularly advantageous. In this procedure, the zeolites in the form of extrudates, pellets or fluidizable material are impregnated with aqueous $NaH_2PO_4$ solution, dried at 110° C. and calcined at 500° C.

The catalysts described here may alternatively be used in the form of 2-4 mm extrudates, pellets having a diameter of from 3 to 5 mm or chips having particle sizes of from 0.1 to 0.5 mm or as a fluidized catalyst.

The following reaction conditions are chosen for the novel process:

The reaction is advantageously carried out in the gas phase at from 100° to 500° C., in particular from 150° to 350° C., and under from 0.1 to 100, in particular from 0.5 to 10, bar. In the reaction in the gas phase, it is advantageous to maintain a weight hourly space velocity (WHSV) of from 0.1 to 20, in particular from 1 to 10, g of starting material of the formula II per g of catalyst per hour. The gas-phase reaction can be carried out in a fixed bed or in a fluidized bed. It is also possible to carry out the reaction in the liquid phase (suspension, trickle-bed or liquid-phase method) at from 50° to 200° C. The reaction may be effected batchwise or, preferably, continuously. The use of reduced pressure may be particularly advantageous.

Sparingly volatile or solid starting materials are used in dissolved form, for example in solution in tetrahydrofuran, toluene or petroleum ether. In general, the educt may be diluted with solvents of this type or with inert gases, such as $N_2$, Ar or steam.

After the reaction, the resulting products are isolated from the reaction mixture by a conventional method, for example by distillation; unconverted starting materials are, if desired, recycled to the reaction.

In this procedure, gaseous reaction products are immediately introduced into a separation stage and are separated into their individual components, for example in a fractionating column. In a preferred embodiment, the reacted mixtures are quenched in an aqueous bicarbonate solution, e.g. $KHCO_3$ or $NaHCO_3/Na_2SO_4$.

EXAMPLES 1-16

The reactions in the gas phase are carried out under isothermal conditions in a tube reactor (coil, 0.6 cm internal diameter, 90 cm length) for not less than 6 hours. The reaction products are isolated and characterized by conventional methods, quantitative determination of the reaction products and of the starting materials is effected by a known gas chromatography method.

The catalysts used for the novel process are:

Catalyst A

The borosilicate zeolite of the pentasil type is prepared in a hydrothermal synthesis from 640 g of finely divided $SiO_2$, 122 g of $H_3BO_3$ and 8,000 g of an aqueous 1,6-hexanediamine solution (weight ratio 50:50) at 170° C. under autogenous pressure in a stirred autoclave. The crystalline reaction product is filtered off, washed thoroughly, dried at 100° C. for 24 hours and then calcined at 500° C. for 24 hours. This borosilicate zeolite is composed of 94.2% by weight of $SiO_2$ and 2.3% by weight of $B_2O_hd 3$.

This material is molded with a molding assistant to give 2 mm extrudates, which are dried at 110° C. for 16 hours and calcined at 500° C. for 24 hours.

Catalyst B

The iron silicate zeolite of the pentasil type is synthesized under hydrothermal conditions, under autogenous pressure and at 165° C., from 273 g of waterglass, dissolved in 253 g of an aqueous, 1,6-hexanediamine solution (weight ratio 50:50), and 31 g of iron sulfate, dissolved in 21 g of 96% strength sulfuric acid and 425 g of water, in a stirred autoclave in the course of 4 days. The zeolite is filtered off, washed thoroughly, dried at 110° C. for 24 hours and calcined at 500° C. for 24 hours. The resulting iron silicate zeolite has an $SiO_2/Fe_2O_3$ ratio of 17.7 and an $Na_2O$ content of 1.2% by weight. This zeolite is molded with finely divided $SiO_2$ in a weight ratio of 80:20 to give 2.5 mm extrudates, which are dried at 110° C. for 16 hours and calcined at 500° C. for 24 hours.

Catalyst C

Catalyst A is impregnated with aqueous $Ce(NO_3)_{33}$ solution, dried at 130° C. for 2 hours and calcined at 540° C. for 2 hours. The Ce content is 1.8% by weight.

The experimental results and the reaction conditions are summarized in the Table below.

Reaction (A) 1,1-dimethoxyethane→methyl vinyl ether+methanol

Reaction (B) 1,1-dimethoxy-1-methylpropane→1-methoxy-2-methylprop-1-ene+methanol Reaction (C) 1,1-di-isopropoxybutane→1-isopropoxy-but-1-ene +isopropanol diluted 75:25 with THF Reaction (D) 1,1-dimethoxyoctane→1-dimethoxyoct-1-ene+methanol diluted 75:25 with THF Reaction (E) 1,1-dimethoxy-2-phenylethane→1-methoxystyrene+methanol diluted 50:50 with THF Reaction (F) 1,1-dimethoxy-2-[p-fluorophenyl]-ethane→1-methoxy-p-fluorostyrene+methanol diluted 50:50 with THF Reaction (G) 1-phenyl-1,1-dimethoxyethane→1-phenyl-1-methoxyethane+methanol diluted 50:50 with THF Reaction (H) Cyclohexanone diethyl ketal→cyclohexenyl ethyl ether+ethanol diluted 50:50 with THF The dilution is stated in % by weight.

EXAMPLE 17

200 ml/h of 98% pure 1,1-dimethoxyoctane are vaporized in a stream of 300 ml/h of nitrogen and are passed, at 300° C., over 1 l of the borosilicate zeolite catalyst A, which is present in a reaction tube electrically heated from the outside.

The gaseous reaction mixture is passed into the middle part of a fractionating column, and the methanol formed and other low boilers distill off at the top while the 1-methoxyoct-1-ene can be taken off at the bottom of the column.

Purification may be effected in a simple manner by a conventional distillation.

The conversion of 1,1-dimethoxyethane is complete, and the yield is 94.4% of theory.

Catalyst A still shows no signs of deactivation after a reaction time of 120 hours.

EXAMPLE 18

The procedure described in Example 17 is followed, except that 80 ml/h of a 50% strength solution of 1,1-dimethoxy-2-phenylethane solution in tetrahydrofuran is reacted at 230° C.

The yield of methyl styrene ether is 93.9% of theory at a conversion of 100%.

EXAMPLE 19

The procedure described in Example 17 is followed, except that 80 ml/h of a 50% strength solution of hexyldimethoxymethane in tetrahydrofuran are reacted at 230° C.

The yield of cyclohexanemethylene methyl ether is 85.5% of theory at a conversion of 100%.

EXAMPLE 20

The procedure described in Example 17 is followed, except that 120 ml/h of a 50% strength solution of 1,1-diethoxy-3-chloropropane in tetrahydrofuran are reacted at The yield of 1-methoxy-3-chloroprop-1-ene is 70.5% of theory at a conversion of 100%.

TABLE 1

| | Example | | | | | | | | | | | | | | | |
|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 |
| Reaction | (A) | (A) | (B) | (B) | (B) | (C) | (C) | (D) | (D) | (E) | (E) | (E) | (F) | (F) | (G) | (H) |
| Catalyst | A | B | A | C | B | A | B | A | C | A | A | B | A | C | A | A |
| Temperature °C. | 300 | 300 | 300 | 300 | 300 | 300 | 300 | 300 | 300 | 250 | 300 | 300 | 300 | 300 | 300 | 300 |
| WHSV h$^{-1}$ | 2 | 2 | 2 | 2 | 2 | 2 | 2 | 2 | 2 | 3 | 3 | 3 | 3 | 3 | 3 | 3 |
| Conversion (II) % | 100 | 100 | 100 | 100 | 100 | 100 | 100 | 100 | 100 | 100 | 100 | 100 | 100 | 100 | 100 | 100 |
| Selectivity (I) % | 95.6 | 93.7 | 92.8 | 93.5 | 89.7 | 92.2 | 87.7 | 94.2 | 92.6 | 95.4 | 92.4 | 88.7 | 90.1 | 92.7 | 95.7 | 87.2 |

We claim:

1. A process for the preparation of a vinyl ether of the formula (I)

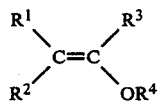

(I)

where $R^1$ to $R^3$ are identical or different and are each hydrogen, a straight-chain or branched alkyl or alkenyl radical of not more than 12 carbon atoms, halogen-substituted alkyl, a cycloalkyl or cycloalkenyl radical of 5 to 8 carbon atoms, an aryl, alkylaryl, alkenylaryl, aralkyl or aralkenyl radical of 6 to 16 carbon atoms or a halogen-substituted aryl and furthermore $R^1$ and $R^2$ or $R^1$ and $R^3$, together with the carbon atom to which they are bonded, may form a cycloalkane or cycloalkene, and $R^4$ is alkyl, alkylaryl or aralkyl which process comprises: eliminating an alcohol from an acetal or ketal of the formula (II)

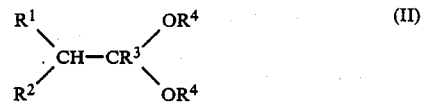

(II)

where $R^1$ to $R^4$ have the above meanings, in the presence of a borosilicate zeolite having a pentasil structure or an iron silicate zeolite having a pentasil structure as a catalyst.

2. The process of claim 1, wherein the borosilicate and/or iron silicate zeolites are synthesized from aqueous amine solutions containing at least two amino groups per molecule.

3. The process of claim 1, wherein the reaction is carried out in the gas phase at from 100° to 500° C.

* * * * *